United States Patent
Rauh

(10) Patent No.: US 9,998,657 B2
(45) Date of Patent: Jun. 12, 2018

(54) SUPPORT SYSTEM FOR THE MANUFACTURE OF DENTAL RESTORATIONS

(71) Applicant: Vita Zahnfabrik H. Rauter GmbH & Co. KG, Bad Saeckingen (DE)

(72) Inventor: Wolfgang Rauh, Bad Saeckingen (DE)

(73) Assignee: VITA ZAHNFABRIK H. RAUTER GMBH & CO. KG, Bad Saeckingen (DE)

( * ) Notice: Subject to any disclaimer, the term of this patent is extended or adjusted under 35 U.S.C. 154(b) by 152 days.

(21) Appl. No.: 15/054,881

(22) Filed: Feb. 26, 2016

(65) Prior Publication Data

US 2016/0278890 A1 Sep. 29, 2016

(30) Foreign Application Priority Data

Mar. 28, 2015 (DE) .................... 20 2015 002 371 U

(51) Int. Cl.
*A61B 1/04* (2006.01)
*H04N 5/225* (2006.01)
(Continued)

(52) U.S. Cl.
CPC ..... *H04N 5/23229* (2013.01); *A61B 1/00016* (2013.01); *A61B 1/04* (2013.01);
(Continued)

(58) Field of Classification Search
CPC ......... A61B 1/00016; A61B 1/04; A61B 1/24; A61B 5/0088; A61B 5/1032;
(Continued)

(56) References Cited

U.S. PATENT DOCUMENTS

| 6,309,215 B1* | 10/2001 | Phan ........................ A61C 7/00 433/24 |
| 6,350,120 B1* | 2/2002 | Sachdeva ................. A61C 7/00 433/24 |

(Continued)

OTHER PUBLICATIONS

Quang et al, Dental Intraoral System Supporting Tooth Segmentation, 2013.*

(Continued)

*Primary Examiner* — Shan E Elahi
(74) *Attorney, Agent, or Firm* — Ohlandt, Greeley, Ruggiero & Perle, LLP

(57) ABSTRACT

A support system for the manufacture of dental restorations is provided that includes a measurement device for determining the tooth data, such as the tooth color and color coordinates, and a data processing device including a camera for capturing a tooth image. The data processing device includes a reception module and the measurement device has a transmission module, for direct transmission of measured tooth data from the measurement device to the data processing device. The support system further includes an allocation module integrated into the data processing device for allocating the received tooth data to the tooth image, and a transmission module integrated into the data processing device for transmission of the tooth image inclusive of allocated tooth data to a data processing device of a dental laboratory.

11 Claims, 1 Drawing Sheet

(51) Int. Cl.
*H04N 5/232* (2006.01)
*A61B 1/24* (2006.01)
*A61C 19/04* (2006.01)
*A61B 1/00* (2006.01)
*G06T 7/00* (2017.01)
*A61C 19/10* (2006.01)
*A61B 5/00* (2006.01)
*A61B 5/103* (2006.01)
*G01J 3/50* (2006.01)

(52) U.S. Cl.
CPC ............... *A61B 1/24* (2013.01); *A61C 19/04* (2013.01); *G06T 7/0012* (2013.01); *H04N 5/225* (2013.01); *A61B 5/0088* (2013.01); *A61B 5/1032* (2013.01); *A61C 19/10* (2013.01); *G01J 3/508* (2013.01); *G06T 2207/30036* (2013.01)

(58) Field of Classification Search
CPC ..... A61C 13/0004; A61C 19/04; A61C 19/10; G01J 3/508; G06T 2207/30036; G06T 7/0012; H04N 5/225; H04N 5/23229
USPC .......................................................... 348/77
See application file for complete search history.

(56) References Cited

U.S. PATENT DOCUMENTS

| | | | | |
|---|---|---|---|---|
| 6,575,751 | B1* | 6/2003 | Lehmann | G16H 50/50 433/223 |
| 7,474,307 | B2* | 1/2009 | Chishti | A61C 7/00 345/20 |
| 8,105,080 | B2* | 1/2012 | Chishti | A61C 7/00 433/24 |
| 8,790,118 | B2* | 7/2014 | Lehmann | A61C 13/0004 433/223 |
| 8,950,742 | B2* | 2/2015 | Parker | A61C 7/002 269/287 |
| 2002/0072027 | A1* | 6/2002 | Chishti | A61C 7/00 433/24 |
| 2003/0224311 | A1* | 12/2003 | Cronauer | A61C 7/08 433/6 |
| 2004/0197727 | A1* | 10/2004 | Sachdeva | A61C 7/00 433/24 |
| 2004/0252303 | A1* | 12/2004 | Giorgianni | G01J 3/50 356/402 |
| 2005/0055118 | A1* | 3/2005 | Nikolskiy | G06F 19/321 700/98 |
| 2006/0286501 | A1* | 12/2006 | Chishti | A61C 7/00 433/24 |
| 2007/0026363 | A1* | 2/2007 | Lehmann | A61C 13/0004 433/223 |
| 2008/0284902 | A1 | 11/2008 | Konno et al. | |
| 2008/0305451 | A1* | 12/2008 | Kitching | A61C 7/00 433/24 |
| 2009/0168063 | A1* | 7/2009 | Kobayashi | A61C 19/10 356/404 |
| 2010/0141931 | A1* | 6/2010 | Ramirez Mancilla | G01B 11/0625 356/51 |
| 2012/0100508 | A1* | 4/2012 | Lehmann | G16H 50/50 433/223 |
| 2012/0221135 | A1* | 8/2012 | Kim | A61C 9/0046 700/98 |
| 2012/0231421 | A1* | 9/2012 | Boerjes | A61B 5/4547 433/223 |
| 2013/0209954 | A1* | 8/2013 | Prakash | A61B 1/0005 433/29 |
| 2014/0200865 | A1* | 7/2014 | Lehmann | A61C 13/0004 703/1 |
| 2014/0356798 | A1* | 12/2014 | Parker | A61C 7/002 433/2 |
| 2017/0312058 | A1* | 11/2017 | Fisker | A61C 13/0004 |

OTHER PUBLICATIONS

Wang et al, A computer-Aided Analysis on Dental Prosthesis Shade Matching, 2011.*
Bae et al, Comparison of a digital color and hyper-spectral camera for dental plaque detection, 2007.*

* cited by examiner

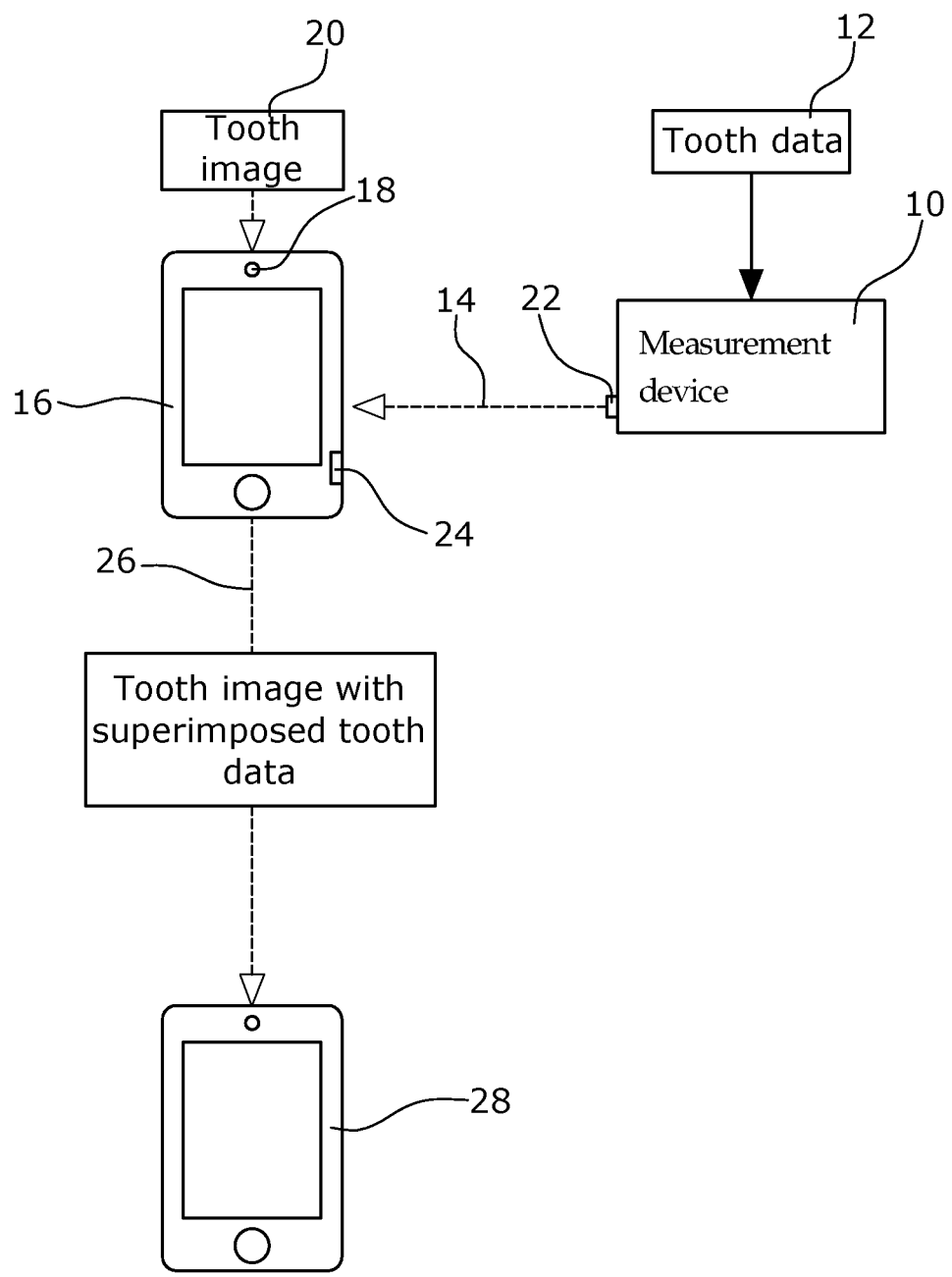

SUPPORT SYSTEM FOR THE MANUFACTURE OF DENTAL RESTORATIONS

BACKGROUND

1. Field of the Disclosure

The present disclosure relates to a support system for the manufacture of dental restorations.

2. Discussion of the Background Art

For the manufacture of dental restorations, it is first required that the dentist will determine tooth data of the tooth that is to be restored. These tooth data include also the tooth color. The tooth color is typically communicated by indication of a color pattern from a dental color system (e.g. VITA classical A1-D4 or VITA System 3D-Master); in the ideal case, this indication is supplemented by brightness, chroma and shade of color as color coordinates, thus allowing for a more precise description of the tooth color. Determination of the tooth color and of the color coordinates can be performed with the aid of suitable measurement devices. A useful device for this purpose is the measurement device VITA Easyshade® of VITA Zahnfabrik company. In a next step, it is required to generate a photographic image of the corresponding tooth of the patient. Presently, such a tooth image is generated by means of a digital camera. Then, the generated tooth image as well as the tooth data determined by the measurement device have to be transmitted to a computer. With the aid of special software installed on the computer, the tooth data will then be allocated to the tooth image. Such an allocation process can be performed e.g. by use of the software VITA Assist and VITA ShadeAssist. This allocating has to be carried out by the dentist. In the allocation process, errors may occur e.g. due to selection of a wrong tooth image. Next, the tooth image with the allocated tooth data will be transmitted to a dental laboratory, particularly via Internet. The dental technician will then have to call up the data received from the data processing device of the dental laboratory, optionally further process these data and then, for performing the dental restoration, print them out. This has the disadvantage that the acceptance of this system on the dental technician's side is often low.

It is an object of the disclosure to provide a support system for the manufacture of dental restorations which allows for improved handling and preferably also will find better acceptance.

SUMMARY

The support system for the manufacture of dental restorations as provided by the present disclosure comprises a measurement device for preferably automatic measurement of tooth data. The tooth data comprise particularly the tooth color as well as the color coordinates brightness, chroma and shade of color. The support system further comprises a data processing device provided with a camera for capturing a tooth image. According to a particularly preferred embodiment, said data processing device is a mobile data processing device such as e.g. a mobile phone, particularly a smart phone or a tablet computer. Using such a data processing device, it is possible, on the one hand, to capture a tooth image of the to-be-restored-teeth with the aid of the camera and, on the other hand, to process data. For this purpose, the data processing device comprises a reception module, and the measurement device comprises a transmission module for direct communication of measured tooth data from the measurement device to the data processing device.

According to the disclosure, the data processing device comprises an integrated allocation module. The allocation module is preferably realized by corresponding software which can be realized e.g. in form of an app. The allocation module serves for allocating the received tooth data to the tooth image recorded by the data processing device itself. Accordingly, to the person operating the support system, particularly the dentist, allocation will be extremely simple and reliable. Thus, for instance, the dentist can first acquire the tooth data, directly transfer them to the mobile phone or the like and, particularly, then capture a tooth image so that the tooth data will be directly allocated to the tooth image. Thereby, allocation errors are excluded. Further, of course, it is possible to first capture the tooth image and then to transfer the tooth data to the mobile phone or the like so that, also in this case, there is achieved an unambiguous allocation. To the operator, particularly the dentist, the handling will thus be noticeably facilitated. The step of transmitting the tooth image to a computer is eliminated. Also the need for allocating the transmitted tooth image to the tooth data, likewise transmitted to the computer, is eliminated. Particularly, there is no need anymore for a computer with corresponding software for allocating the data.

The tooth data and the data of the tooth image, which data have been stored in the data processing device such as e.g. the mobile phone and have been allocated to each other, can be transmitted in a simple manner e.g. from the mobile phone—via a transmission module which anyway is provided in said phone—to a data processing device of a dental laboratory. Particularly, it is of advantage that this can be carried out immediately after the allocating of the data sets, e.g. on the mobile phone by the dentist.

It is particularly preferred that also the data processing device of the dental laboratory is a mobile phone, a tablet computer or the like. Also on the receiver side, i.e. for the technician in the dental laboratory, the handling is distinctly facilitated. The dental technician will receive the corresponding data directly on his/her mobile phone, tablet or the like. Such a reception device will facilitate the handling. In so far, the acceptance of such devices is will be much higher.

In order to realize the communication between the devices in a most simple manner, it is particularly preferred that the data transmission between the measurement device and the data processing device such as the mobile phone or the is performed wirelessly. Particularly, this can be carried out via an NFC interface, Bluetooth or WLAN.

Particularly for bidirectional data exchange and/or data matching, it is further preferred that both the measurement device and the data processing device such as e.g. the mobile phone comprise a transmission and reception module so as to allow for wireless communication between the two devices.

Data transmission to the data processing device of the dental laboratory is preferably carried out by remote data transmission, particularly via the mobile phone network.

The disclosure will be explained in greater detail hereunder by way of a preferred embodiment with reference to the accompanying drawing.

BRIEF DESCRIPTION OF THE DRAWING

The sole FIGURE of the drawing is a schematic representation of a preferred embodiment of the support system of the manufacture of dental restorations according to the disclosure.

DETAILED DESCRIPTION OF THE PREFERRED EMBODIMENT

The support system of the manufacture of dental restorations according to the disclosure and shown in the FIGURE comprises a measurement device 10. With the aid of this measurement device, tooth data 12 will be detected particularly by the dentist. Said tooth data, optionally processed or treated in measurement device 10, will be transmitted to a data processing device such as e.g. mobile phone 16, preferably via a Bluetooth connection 14. Prior to or after transmission of the tooth data, a tooth image 20 is generated with the aid of said mobile phone by use of the camera 18 integrated into mobile phone 16.

With the aid of software or an app provided in mobile phone 16, the transmitted tooth data 12 will be allocated to the captured tooth image 20.

For data transmission between mobile phone 16 and measurement device 10, measurement device 10 preferably comprises a transmission/reception device 22, and also mobile phone 16 comprises an integrated transmission/reception device 24. Thereby, data exchange in both directions and respectively data matching are rendered possible.

Then, via the conventional transmission module integrated into mobile phone 16, the tooth image together with the allocated tooth data will be transmitted e.g. via a mobile phone network 26 to a data processing device of a dental laboratory, which device preferably is again provided in the form of a mobile phone 28.

Although the disclosure has been described and illustrated with reference to specific illustrative embodiments thereof, it is not intended that the disclosure be limited to those illustrative embodiments. Those skilled in the art will recognize that variations and modifications can be made without departing from the true scope of the disclosure as defined by the claims that follow. It is therefore intended to include within the disclosure all such variations and modifications as fall within the scope of the appended claims and equivalents thereof.

What is claimed is:

1. A support system for the manufacture of dental restorations, comprising:
   a measurement device for determining the tooth data,
   a data processing device including a camera for capturing a tooth image,
   the data processing device comprising a first reception module and the measurement device comprising a first transmission module, for direct transmission of the tooth data from the measurement device to the data processing device,
   an allocation module integrated into the data processing device for allocating the tooth data to the tooth image, and
   a second transmission module integrated into the data processing device for transmission of the tooth image having the tooth data allocated thereto to a data processing device of a dental laboratory.

2. The support system according to claim 1, wherein, using the measurement device, automatic data acquisition of at least a part of the tooth data is performed.

3. The support system according to claim 1, wherein the camera is integrated into the data processing device.

4. The support system according to claim 1, wherein the data processing device is designed as mobile data processing device.

5. The support system according to claim 1, wherein the measurement device and the data processing device transmit the tooth data and the tooth image wirelessly.

6. The support system according to claim 1, wherein, for data exchange from the data processing device to the measurement device and/or for data matching, the measurement device comprises a second reception module.

7. The support system according to claim 1, wherein the second transmission module of the data processing device for data transmission to the data processing device of the dental laboratory is designed for remote data transmission.

8. The support system according to claim 5, wherein the measurement device and the data processing device transmit the tooth data and the tooth image wirelessly using at least one selected from the group consisting of: NFC communication, Bluetooth and WLAN.

9. The support system according to claim 7, wherein the remote data transmission is a mobile phone network.

10. The support system according to claim 1, wherein the tooth data comprises tooth color and color coordinates.

11. The support system according to claim 4, wherein the mobile data processing device is a mobile phone or a tablet.

* * * * *